United States Patent [19]
LaPack et al.

[11] Patent Number: 5,019,139
[45] Date of Patent: May 28, 1991

[54] VALVE MEMBRANE COMBINATION

[75] Inventors: Mark A. LaPack; James C. Tou, both of Midland, Mich.

[73] Assignee: The Dow Chemical Company, Midland, Mich.

[21] Appl. No.: 455,472

[22] Filed: Dec. 22, 1989

[51] Int. Cl.$^5$ ............................................. B01D 53/22
[52] U.S. Cl. .......................................... 55/158; 66/56; 66/5
[58] Field of Search ..................................... 55/16, 158

[56] References Cited
U.S. PATENT DOCUMENTS

| | | | |
|---|---|---|---|
| 1,174,631 | 3/1916 | Snelling | 55/158 |
| 2,045,379 | 6/1936 | Bennett | 55/158 X |
| 2,964,124 | 12/1960 | Peierls et al. | 55/158 |
| 3,421,292 | 1/1969 | Llewellyn | 55/158 |
| 3,494,174 | 2/1970 | Green et al. | 55/158 X |
| 3,638,401 | 2/1972 | Kabler | 55/158 |
| 3,662,520 | 5/1972 | Saunders | 55/158 |
| 3,668,837 | 6/1972 | Gross | 55/158 |
| 3,721,065 | 3/1973 | Robicheaux et al. | 55/16 X |
| 4,003,725 | 1/1977 | Bunn, Jr. et al. | 55/158 |
| 4,808,199 | 2/1989 | Yearout | 55/158 X |

Primary Examiner—Robert Spitzer
Attorney, Agent, or Firm—Timothy S. Stevens

[57] ABSTRACT

A combination of a membrane, such as a silicone rubber membrane, and a valve having a chamber within it, such as a solenoid valve. The present invention is suitable, for example, for use with a mass spectrometer. The membrane partitions the chamber into a first chamber portion and a second chamber portion. The valve has at least three passageways into it. The first two passageways lead to the first chamber portion. The third passageway leads to the second chamber portion. A solenoid plunger is used to close off the third passageway when desired. When used with a mass spectrometer, the third passageway is connected to the vacuum inlet of the mass spectrometer and a sample is flowed into and out of the first chamber portion via the first two passaageways. A component of interest in the sample can permeate across the membrane into the second chamber portion and can flow via the third passageway to the mass spectrometer. When desired, the plunger can be used to close the third passageway.

19 Claims, 3 Drawing Sheets

VALVE MEMBRANE COMBINATION

FIELD OF THE INVENTION

The invention is in the field of chemical analysis and more specifically in the field of valves used with membranes in chemical analysis systems.

BACKGROUND OF THE INVENTION

Membrane cells are used in chemical analysis to partition a sample contained on one side of a membrane from a compartment positioned on the other side of the membrane The sample contains a component of interest that permeates across the membrane into the compartment. The contents of the compartment can then be analyzed for the component of interest. If the sample contains another component that does not permeate across the membrane which otherwise would interfere with the analysis of the component of interest, then the use of a membrane cell in the analysis of the component of interest is beneficial.

Membrane cells can incorporate sheet type membranes and tubular type membranes. A cell using a sheet type membrane can be made by clamping the membrane between two blocks, each block having a cavity machined into it exposed to the membrane, the cavities being juxtaposed across the membrane so that a sample can be placed in one of the cavities with the contents of the other cavity being analyzed for the component of interest that has permeated across the membrane. A cell using a tubular membrane can be made by sealing the ends of a tubular membrane inside and to the ends of a metal tube leaving an annular space between the central portion of the inside of the metal tube and the central portion of the outside of the tubular membrane so that a sample can be placed in the annular space with the contents of the bore of the membrane being analyzed, or conversely, the sample can be placed in the bore of the tubular membrane with the contents of the annular space being analyzed.

One important application of membranes in chemical analysis is in the field of mass spectrometry. The membrane of a membrane cell is used to partition a sample from the vacuum inlet of a mass spectrometer. A component of interest of the sample permeates across the membrane, evaporates into the vacuum on the other side of the membrane and is carried into the mass spectrometer for analysis Usually, a valve is placed in the vacuum line between the membrane cell and the mass spectrometer so that passage of the component of interest into the mass spectrometer can be stopped if desired. Frequently, several membrane cells are connected to a mass spectrometer through such valves so that each can be respectively analyzed in turn. It would be an advance in this art if the valve and the membrane cell could be combined into one unit to reduce the number of apparatus components needed.

SUMMARY OF THE INVENTION

The present invention is a combination of the membrane cell and the valve into a single device which incorporates a selectively permeable membrane having a first side and a second side, such as a sheet type membrane or a tubular membrane. The device has body defining a cavity within it which is partitioned into a first and a second portion by the membrane. The first side of the membrane is exposed to the first cavity portion and the second side of the membrane is exposed to the second cavity portion. The body has three passageways into it. The first passageway leads from the exterior of the body to the first cavity portion. The second passageway also leads from the exterior of the body to the first cavity portion. The third passageway leads from the exterior of the body to the second cavity portion. Finally, a means is provided to controllably close the third passageway, such as a solenoid actuated plunger.

When used in a mass spectrometry system, the third passageway is connected to the vacuum inlet of the mass spectrometer. A sample is flowed into the first passageway, into the first cavity portion, where it comes into contact with the membrane, and then out the second passageway. When the third passageway is open, a component of the sample that permeates across the membrane, evaporates into the second cavity portion and flows into the vacuum inlet of the mass spectrometer.

DETAILED DESCRIPTION OF THE INVENTION

Figure 1:
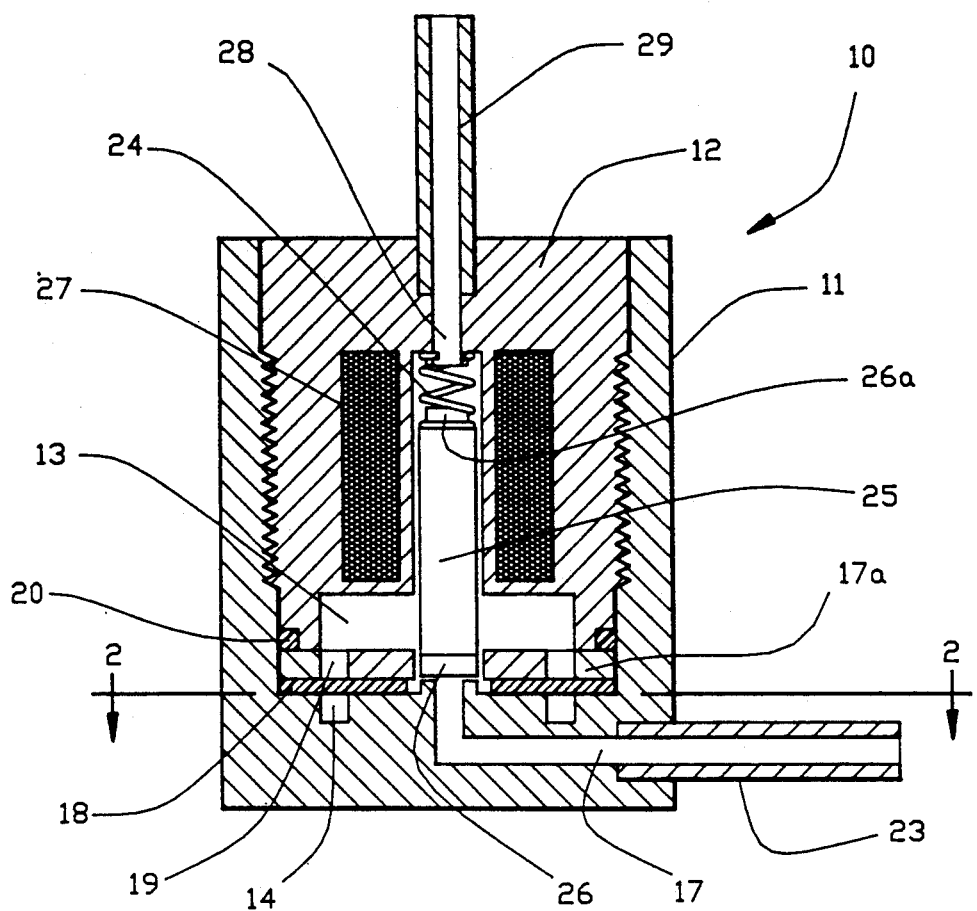
FIG. 1 is a cross-sectional side view of a valve according to the present invention, the valve incorporating a sheet type membrane.
Figure 2:
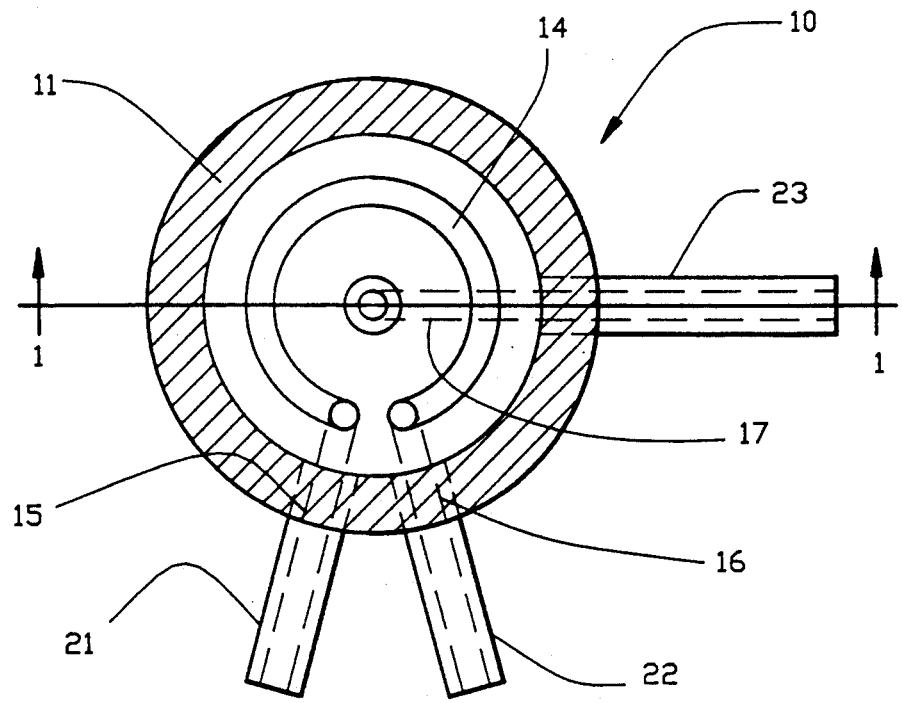
FIG. 2 is a cross-sectional top view of the valve shown in FIG. 1.

Referring now to FIG. 1 and 2, therein is shown a valve 10 incorporating a case 11 and a plug 12. The case 11 and the plug 12 form the body of the valve 10 and define a cavity 13 therein. The case 11 and the plug 12 are preferably made from stainless steel but can be made of almost any other suitable material such as another metal, a ceramic or a polymer. The case 11 has a circular channel 14 machined in it. However, the geometry of such a channel in the present invention is not critical and it could have been made in a spiral shape, a zig-zag shape, a rectangular or other shape. The case 11 has a first passageway 15 from the exterior of the case 11 to one end of the channel 14. The case 11 also has a second passageway 16 from the exterior of the case 11 to the other end of the channel 14. The case 11 further has a third passageway 17 from the exterior of the case 11 to the chamber 13. A washer 17a and a sheet membrane 18 are sandwiched between the plug 12 and the case 11. A series of holes 19 are drilled in the washer 17a opposite the channel 14. An O-ring 20 seals the washer 17a, the case 11 and the plug 12. One side of the membrane 18 is thus exposed to the chamber 13 via the holes 19 while the other side of the membrane 18 is exposed to the channel 14. When the plug 12 is screwed into the case 11, the plug 12 presses on the washer 17a which in turn presses on the membrane 18 which in turn presses on the surface of the chamber 13 adjacent the channel 14 and thereby forms a continuous seal between the membrane 18 and the surface of the chamber 13 adjacent the channel 14. This is important since in the present invention only membrane permeation communication between the channel 14 and the chamber 13 is desirable. A section of stainless steel tubing 21 is brazed to the case 11 to extend the first passageway 15 and the tubing 21 is a part of the valve body according to the present invention. A section of stainless steel tubing 22 is also brazed to the case 11 to extend the second passageway 16 and the tubing 22 is a part of the valve body according to the present invention. A section of stainless steel tubing 23 is also brazed to the case 11 to extend the third passageway 17 and the tubing 23 is a part of the valve body according to the present invention. A coil spring 24 presses a solenoid plunger 25 and a resilient seal 26 against the portion of the case 11 where the third passageway terminates in the chamber 13 closing the third passageway 17. The case 11 further has an fourth passageway 28 from the exterior of the case 11 to the chamber 13. A section of stainless steel tubing 29 is brazed to the case 11 to extend the passageway 28. A resilient seal 26a is shown on the top of the plunger 25. A solenoid coil 27, when energized, pulls the plunger 25 and the seal 26 upward opening the third passageway 17 and closing the fourth passageway 28. Although the valve 10 is shown as a solenoid valve it should be understood that this is not critical in the present invention and that most any valve means can be used to controllably close the fourth and/or third passageways including a manually actuated valve, a pneumatically actuated valve or even a piezoelectrically operated valve.

To use the valve 10 in a mass spectrometry system, the tubing 29 is connected to a vacuum pump and a sample containing a component that permeates across the membrane 18 is flowed into the tubing 21, through the channel 14 and out the tubing 22 while the vacuum inlet of the mass spectrometer is connected to the tubing 23. When the solenoid coil 27 is energized, the component of interest that permeates the membrane 18 into the chamber 13 can flow through the passageway 17 into the mass spectrometer. Connecting a vacuum pump to the tubing 29 is preferred in this application to prevent a pressure surge into the mass spectrometer when the solenoid coil 27 is energized. Several valves of the present invention can be connected to the vacuum inlet of a mass spectrometer so that each can be analyzed at will. In other uses of the present invention, the fourth passageway 28 is not necessary.

The valve 10 can be adapted from a Model 1X259 solenoid valve from the Kip Solenoid Valve Company, Farmington Conn. 06032. The channel 14, the washer 17a, the passageways 15, 28 and 16, the seals 26/26a and the tubing 21, 22, and 23 need to be added. In some applications, the heat generated by the solenoid coil 27 can be a problem because permeation across the membrane 18 can vary with temperature. A solution to this problem that has been found to be effective is to cool the solenoid coil 27 with coolant pumped through a copper tube coil positioned below the solenoid coil 27. Alternatively, a pneumatically actuated valve can be used.

Figure 3:
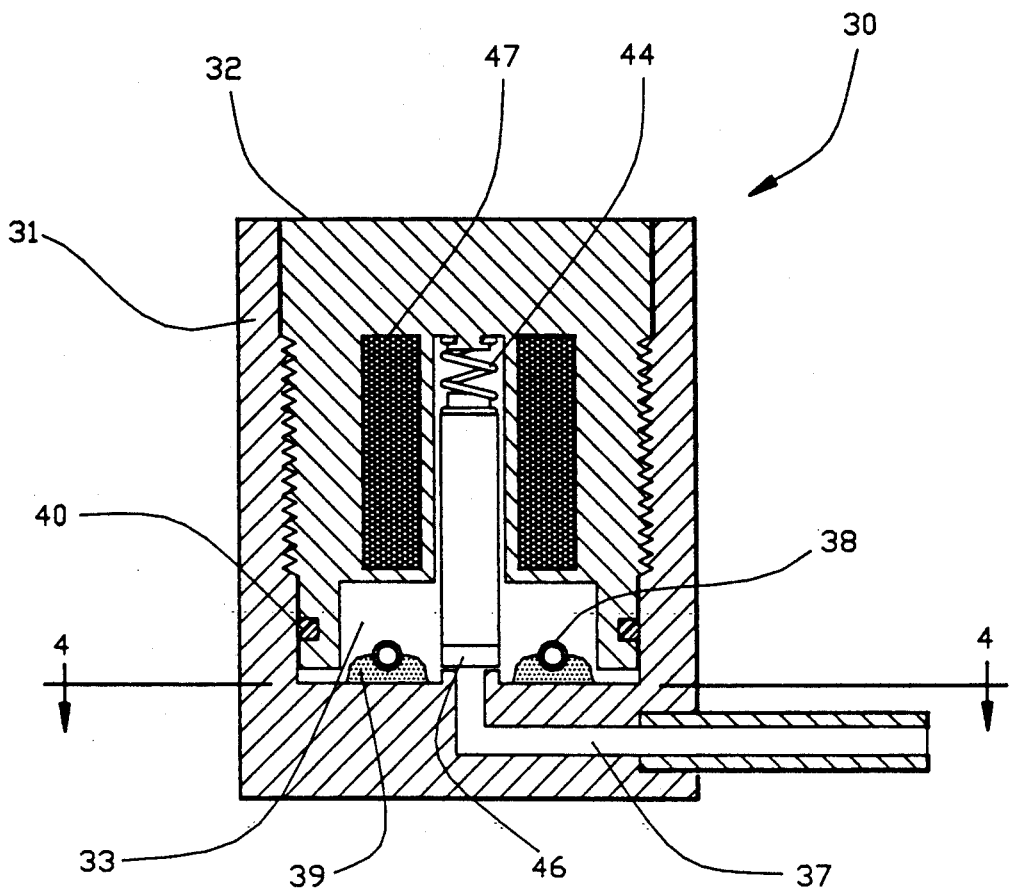
FIG. 3 is a cross-sectional side view of a valve according to the present invention, the valve incorporating a tubular membrane.
Figure 4:
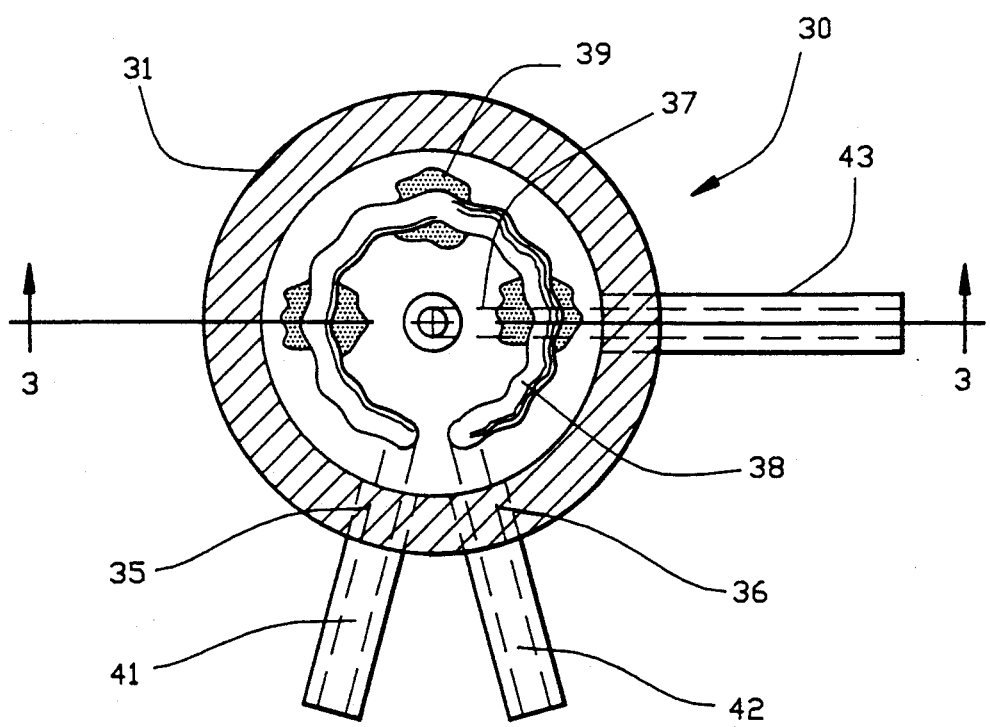
FIG. 4 is a cross-sectional top view of the valve shown in FIG. 3.

Referring now to FIG. 3 and 4, therein is shown a valve 30, similar in many respects to the valve 10 shown in FIG. 1 and 2, incorporating a case 31 and a plug 32. The case 31 and the plug 32 form the body of the valve 30 and define a cavity 33 therein. The case 31 and the plug 32 are made from stainless steel. The case 31 has a first passageway 35 from the exterior of the case 31 to the cavity 33. The case 31 also has a second passageway 36 from the exterior of the case 31 to the chamber 33. The case 31 further has a third passageway 37 from the exterior of the case 31 to the chamber 33. An O-ring 40 seals the case 31 and the plug 32. A tubular membrane 38 is shown with one end portion in the first passageway 35 and the other end portion in the second passageway 36. The end portions of the membrane 38 need to be continuously sealed in the passageways 35 and 36 since in the present invention only membrane permeation communication between the bore of the membrane 38 and the chamber 33 is desirable. Two alternatives for such sealing will be discussed below with reference to FIG. 5 and 6. The central portion of the membrane 38 is secured to the bottom surface of chamber 33 with room temperature vulcanizing silicone rubber sealant 39. A section of stainless steel tubing 41 is brazed to the case 31 to extend the first passageway 35 and the tubing 41 is a part of the valve body according to the present invention. A section of stainless steel tubing 42 is also brazed to the case 31 to extend the second passageway 36 and the tubing 42 is a part of the valve body according to the present invention. A section of stainless steel tubing 43 is also brazed to the case 31 to extend the third passageway 37 and the tubing 43 is a part of the valve body according to the present invention. A coil spring 44 presses a solenoid plunger 45 and a resilient seal 46 against the portion of the case 31 where the third passageway terminates in the chamber 33 closing the third passageway 37. A solenoid coil 47, when energized, pulls the plunger 45 and the seal 46 upward opening the third passageway 37. Although the valve 30 is shown as a solenoid valve it should be understood that this is not at all critical in the present invention and that most any valve can be used to controllably close the third passageway including a manually actuated valve, a pneumatically actuated valve or even a piezoelectrically operated valve.

One use of the valve 30 is in a process for nonequilibrium membrane separation as detailed in the copending application filed on even date herewith.

The valve 30 can be adapted from a Model 1X259 solenoid valve from the Kip Solenoid Valve Company, Farmington Conn. 06032. The passageways 35 and 36, the seal 46 and the tubing 41, 42, and 43 need to be added.

Figure 5:
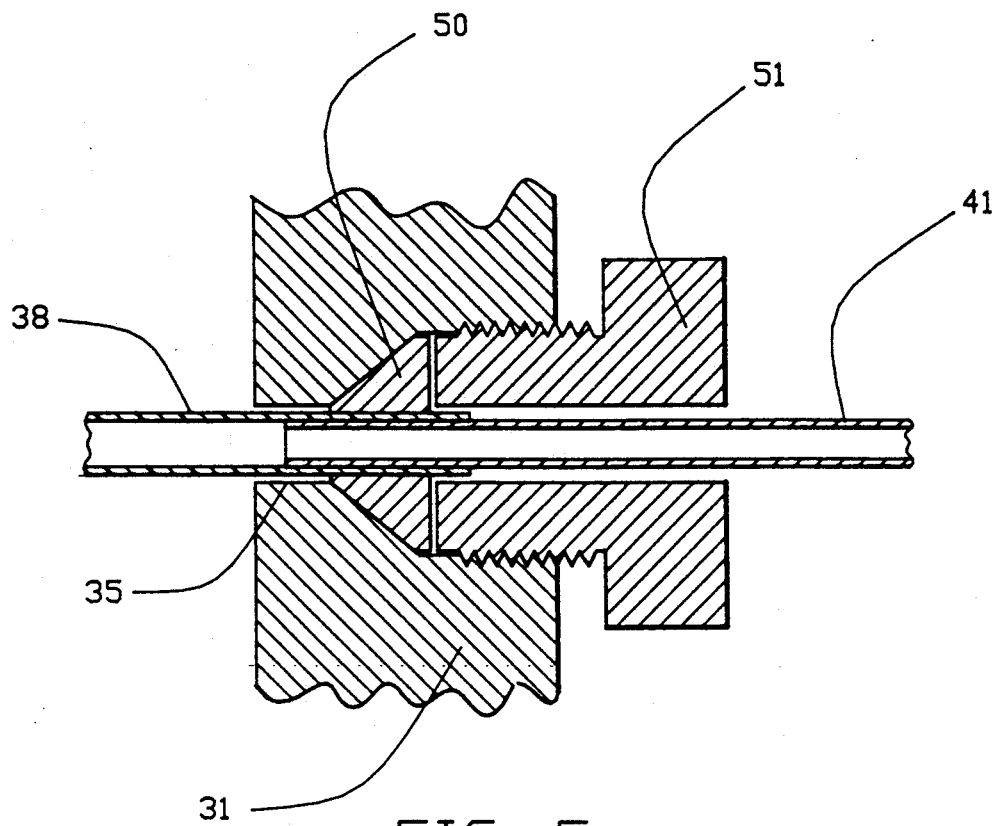
FIG. 5 is a cross-sectional enlarged side view of one means of sealing a tubular membrane to the valve body.
Figure 6:
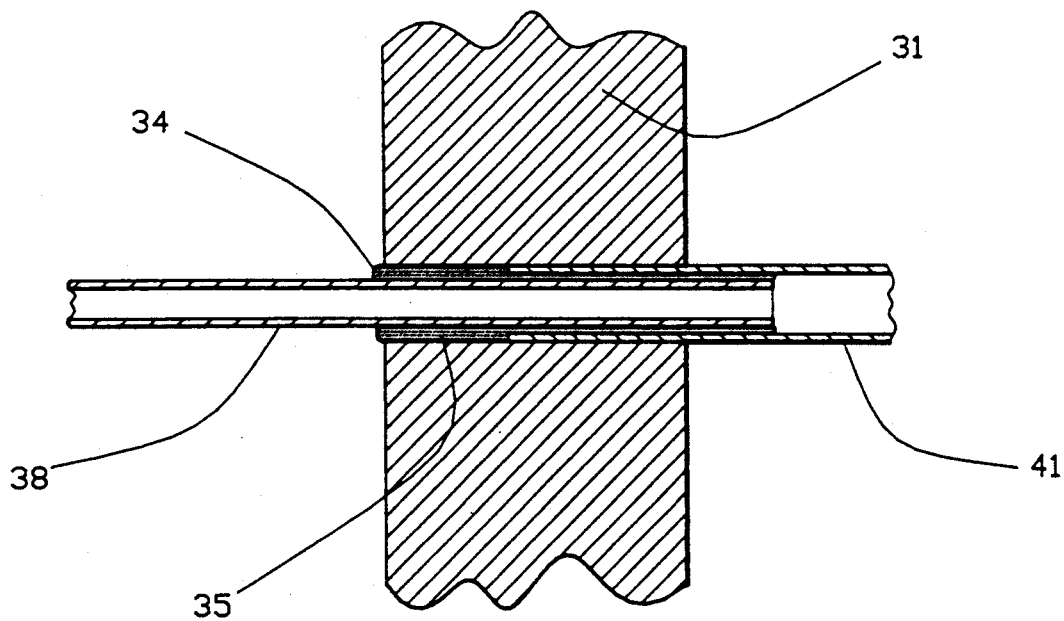
FIG. 6 is a cross-sectional enlarged side view of another means of sealing a tubular membrane to the valve body.

As discussed above in reference to the valve 30 of FIG. 3 and 4, it is important that the membrane 38 be sealed in the passageways 35 and 36. One preferred means of doing this is shown in greater detail in FIG. 6 where room temperature vulcanizing silicone rubber sealant 34 is used to seal the membrane 38 in the passageway 35 and in the tubing 41. A hypodermic needle and syringe can be used to inject the sealant between the membrane 38 and the passageway 35. FIG. 5 shows another alternative for sealing the membrane 38 in the passageway 35 of the case 31. The tube 41 is dimensioned to fit in the bore of the membrane 38 and their juncture is placed within a ferrule 50. A tubing nut 51 compresses the ferrule 50 on the juncture sealing the membrane 38 to the tubing 41. The alternative shown in FIG. 5 allows easier replacement of the membrane 38 in the valve 30.

It should be understood that the apparatus of the present invention can be used in many applications in addition to those mentioned above. For example, it could be used on the inlet of a gas chromatography system to introduce a permeated component of interest into a gas chromatography column or into the injection valve of a gas chromatography system. Additionally, it could be incorporated into a probe inserted directly into the vacuum chamber of a mass spectrometer.

The membrane of the present invention must be a selectively permeable membrane and not an impermeable membrane such as a sheet metal diaphragm of the type that has long been used in valves such as pressure regulation valves. The membrane of the present invention can be nonporous or porous as long as it is selectively permeable to the component of interest, i.e., that the rate of permeation of the component of interest across the membrane be different than the rate of permeation across the membrane of another component. Sheet and tubular membranes of nonporous silicone rubber are preferred examples. Other examples of suitable membrane materials include porous polyethylene membranes (such as Celgard brand sheet or tubular membranes from Celanese), membranes made from polytetrafluoroethylene, polycarbonate, other rubbers and ion exchange polymers (such as Nafion brand ion exchange membranes from DuPont). Many other examples of suitable membranes can be found commercially available or described in publications such as Membranes in Separations by professors Hwang and Kammermeyer published by Krieger in 1984.

The difference between a nonporous and a porous membrane relates to the predominant mechanism of permeation of a component across the membrane. The mechanism of permeation of a component across a nonporous membrane is: (1) sorption of the component into one side of the membrane; (2) diffusion of the component through the membrane to the other side of the membrane; and, (3) desorption of the component from the other side of the membrane. The mechanism of permeation of a component across a porous membrane is: (1) diffusion or flow of the component into a pore of one side of the membrane: (2) diffusion or flow of the component through the pores of the membrane to the other side of the membrane: and, (3) diffusion or flow of the component out of a pore of the other side of the membrane.

What is claimed is:

1. A valve, comprising:
(a) a semipermeable membrane having a first side and a second side;
(b) a body, the body defining a cavity therein, the cavity being partitioned by the membrane into a first cavity portion exposed to the first side of the membrane and a second cavity portion exposed to the second side of the membrane, the body having a first passageway thereinto, the body having a second passageway thereinto, the body having a third passageway thereinto, the first passageway having a first end opening into the first cavity portion and a second end opening to the exterior of the body, the second passageway having a first end opening into the first cavity portion and a second end opening to the exterior of the body, the third passageway having a first end opening into the second cavity portion and a second end opening to the exterior of the body, so that a fluid can be flowed through the first passageway, into the first cavity portion and then through the second passageway, the fluid containing a component that can permeate across the membrane into the second cavity portion and then can flow out of the body through the third passageway; and
(c) means for controllably closing the third passageway so that flow through the third passageway from the second cavity portion can be controllably stopped, the means for controllably closing the third passageway being positioned within the cavity.

2. The valve of claim 1 wherein the means for controllably closing the third passageway includes a solenoid actuated plunger.

3. The valve of claim 2 wherein the body has a fourth passageway and a means for controllably closing the fourth passageway, the fourth passageway having a first end opening into the second cavity portion and a second end opening to the exterior of the body.

4. The valve of claim 3 wherein the means for controllably closing the fourth passageway includes a solenoid actuated plunger.

5. The valve of claim 4 wherein the semipermeable membrane is a semipermeable silicone rubber membrane.

6. The valve of claim 1 wherein the semipermeable membrane is a semipermeable nonporous membrane 7. The valve of claim 6 wherein the semipermeable nonporous membrane is a semipermeable nonporous silicone rubber membrane.

8. A valve, comprising:
(a) a body, the body defining a cavity therein, the body defining a first passageway thereinto, the body defining a second passageway thereinto, the body defining a third passageway thereinto, the first passageway having a first end opening into the cavity and a second end opening to the exterior of the body, the second passageway having a first end opening into the cavity and a second end opening to the exterior of the body, the third passageway having a first end opening into the cavity and a second end opening to the exterior of the body;
(b) a tubular type semipermeable membrane, the membrane having a first end portion, the membrane having a second end portion, the membrane having central portion, the central portion of the membrane being positioned within the cavity, the first end portion of the tubular membrane being continuously sealed within the first passageway, the second end portion of the tubular membrane being continuously sealed within the second passageway, so that a fluid can be flowed through the first passageway, through the bore of the central portion of the membrane and then through the second passageway, the fluid containing a component that can permeate across the membrane into the cavity and then can flow out of the body through the third passageway; and
(c) means for controllably closing the third passageway so that flow through the third passageway from the cavity can be controllably stopped, the means for controllably closing the third passageway being positioned within the cavity.

9. The valve of claim 8 wherein the means for controllably closing the third passageway includes a solenoid actuated plunger.

10. The valve of claim 9 wherein the semipermeable tubular type membrane is a semipermeable tubular type silicone rubber membrane.

11. The valve of claim 8 wherein the semipermeable tubular type membrane is a semipermeable tubular type nonporous membrane.

12. The valve of claim 11 wherein the semipermeable tubular type nonporous membrane is a semipermeable tubular type nonporous silicone rubber membrane.

13. A valve, comprising:
(a) a body, the body defining a cavity therein, the body defining a first passageway thereinto, the body defining a second passageway thereinto, the body defining a third passageway thereinto, the body defining a channel therein, the cavity having a surface, the channel facing the cavity, the first passageway having a first end opening into the channel and a second end opening to the exterior of the body, the second passageway having a first end opening into the channel and a second end opening to the exterior of the body, the third passageway having a first end opening into the cavity and a second end opening to the exterior of the body;
(b) a sheet type semipermeable membrane, the membrane having a first side and a second side, the membrane juxtaposed between the channel and the cavity, the second side of the membrane being exposed to the cavity, the first side of the membrane being exposed to the channel and continuously sealed to the surface of the cavity adjacent the channel, so that a fluid can be flowed through the first passageway, through the channel and then through the second passageway, the fluid containing a component that can permeate across the membrane into the cavity and then can flow out of the valve through the third passageway; and
(c) means for controllably closing the third passageway so that flow through the third passageway can be controllably stopped, the means for controllably closing the third passageway being positioned within the cavity.

14. The valve of claim 13 wherein the means for controllably closing the third passageway includes a solenoid actuated plunger.

15. The valve of claim 14 wherein the body has a fourth passageway and a means for controllably closing the fourth passageway, the fourth passageway having a first end opening into the cavity and a second end opening to the exterior of the body.

16. The valve of claim 15 wherein the means for controllably closing the fourth passageway includes a solenoid actuated plunger.

17. The valve of claim 16 wherein the semipermeable sheet type membrane is a semipermeable sheet type silicone rubber membrane.

18. The valve of claim 13 wherein the semipermeable sheet type membrane is a semipermeable nonporous sheet type membrane.

19. The valve of claim 18 wherein the semipermeable nonporous sheet type membrane is a semipermeable nonporous sheet type silicone rubber membrane.

* * * * *